(12) United States Patent
Wiener

(10) Patent No.: US 7,335,997 B2
(45) Date of Patent: Feb. 26, 2008

(54) SYSTEM FOR CONTROLLING ULTRASONIC CLAMPING AND CUTTING INSTRUMENTS

(75) Inventor: Eitan T. Wiener, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 477 days.

(21) Appl. No.: 11/094,204

(22) Filed: Mar. 31, 2005

(65) Prior Publication Data

US 2006/0229514 A1 Oct. 12, 2006

(51) Int. Cl.
*A61B 17/32* (2006.01)
*H02P 9/04* (2006.01)

(52) U.S. Cl. .................................... 290/1 R; 606/169
(58) Field of Classification Search ............... 290/1 R, 290/1 A, 1 B, 7; 322/22, 24; 606/1, 169
See application file for complete search history.

(56) References Cited

U.S. PATENT DOCUMENTS

| | | | |
|---|---|---|---|
| 4,246,490 A * | 1/1981 | Keramati et al. | 290/1 A |
| 4,371,816 A | 2/1983 | Wieser | |
| 4,731,545 A * | 3/1988 | Lerner et al. | 290/54 |
| 5,520,633 A | 5/1996 | Costin | |
| 5,893,835 A | 4/1999 | Witt et al. | |
| 5,897,569 A * | 4/1999 | Kellogg et al. | 606/169 |
| 5,989,275 A * | 11/1999 | Estabrook et al. | 606/169 |
| 6,053,906 A | 4/2000 | Honda et al. | |
| 6,063,098 A * | 5/2000 | Houser et al. | 606/169 |
| 6,068,647 A * | 5/2000 | Witt et al. | 606/205 |
| 6,458,142 B1 | 10/2002 | Faller et al. | |
| 6,633,234 B2 | 10/2003 | Wiener et al. | |
| 6,679,899 B2 | 1/2004 | Wiener et al. | |
| 7,004,174 B2 * | 2/2006 | Eggers et al. | 128/898 |

\* cited by examiner

*Primary Examiner*—Nicholas Ponomarenko
(74) *Attorney, Agent, or Firm*—Welsh & Flaxman LLC

(57) ABSTRACT

A control system for use with an ultrasonic surgical instrument includes a generator supplying electrical energy to an ultrasonic surgical instrument, the electrical energy supplied by the generator being controlled such that power applied by the instrument is maintained constant once a predetermined pressure threshold is met. The control system operates by assigning a nominal power at which the ultrasonic instrument is to operate and adjusting the current and voltage applied to the ultrasonic surgical instrument so as to maintain the power applied by the ultrasonic surgical instrument at approximately the nominal power.

8 Claims, 3 Drawing Sheets

SYSTEM FOR CONTROLLING ULTRASONIC CLAMPING AND CUTTING INSTRUMENTS

BACKGROUND OF THE INVENTION

1. Field of the Invention

The invention relates to ultrasonic surgical clamping and cutting instruments. More particularly, the invention relates to an improved power limiting mechanism for ultrasonic surgical cutting and clamping instruments.

2. Description of the Prior Art

Ultrasonic instruments are used for the safe and effective treatment of many medical conditions. Ultrasonic instruments are advantageous because they may be used to cut and/or coagulate organic tissue using energy in the form of mechanical vibrations transmitted to a surgical end-effector at ultrasonic frequencies.

Ultrasonic vibrations, when transmitted to organic tissue at suitable energy levels and using a suitable end-effector, may be used to cut and/or dissect tissue. Ultrasonic instruments utilizing solid core technology are particularly advantageous, because of the amount of ultrasonic energy that may be transmitted from the ultrasonic transducer through the waveguide to the surgical end-effector. Such instruments are particularly suited for use in minimally invasive procedures, such as, endoscopic or laparoscopic procedures, where the end-effector is passed through a trocar to reach the surgical site.

Ultrasonic vibration is induced in the surgical end-effector by, for example, an electrically excited transducer that may be constructed of one or more piezoelectric or magneto-resistive elements in the instrument handpiece. Vibrations generated by the transducer are transmitted to the surgical end-effector via an ultrasonic waveguide extending from the transducer section to the surgical end-effector.

Many such ultrasonic surgical instruments are known within the prior art. However, they are highly responsive to the pressure applied by the surgeon. In particular, as the surgeon applies greater pressure, the vibration characteristics of the ultrasonic instrument are altered. In fact, in situations where a surgeon exceeds a predetermined pressure level, the power delivered to the tissue may be too high. This may result in undesired tissue effects, such as poor hemostasis of transacted vessels. Furthermore, it is possible that the surgical instrument might not be equipped to handle the material stress requirements for producing the vibration levels at the high pressure levels, thus resulting in undesirable operation of the instrument. Attempts have been made to remedy problems associated with the application of different pressures, for example, by the inclusion of springs within the actuation assembly to mechanically attempt to control applied pressure. However, these attempts have been met with only limited success.

As such, a device is needed wherein a constant power profile is achieved despite personal preferences in the force applied by the surgeon. The present invention provides such a device.

SUMMARY OF THE INVENTION

It is, therefore, an object of the present invention to provide a control system for use with an ultrasonic surgical instrument. The control system includes a generator supplying electrical energy to an ultrasonic surgical instrument, the electrical energy supplied by the generator being controlled such that power applied by the instrument is maintained constant once a predetermined pressure threshold is met.

It is also an object of the present invention to provide an ultrasonic surgical system. The ultrasonic surgical system includes an instrument and an ultrasonic signal generator linked to the instrument for supplying a desired signal to the instrument. The instrument includes an ultrasonic transducer, a housing and an end effector. The ultrasonic signal generator includes a control system. The control system includes a generator supplying electrical energy to the instrument, the electrical energy supplied by the generator being controlled such that power applied by the instrument is maintained constant once a predetermined pressure threshold is met.

It is another object of the present invention to provide a method for controlling the application of power by an ultrasonic surgical instrument. The method is achieved by assigning a nominal power at which the ultrasonic instrument is to operate and adjusting the current and voltage applied to the ultrasonic surgical instrument so as to maintain the power applied by the ultrasonic surgical instrument at approximately the nominal power.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiment of the present invention is disclosed herein. It should be understood, however, that the disclosed embodiment is merely exemplary of the invention, which may be embodied in various forms. Therefore, the details disclosed herein are not to be interpreted as limited, but merely as the basis for the claims and as a basis for teaching one skilled in the art how to make and/or use the invention.

Figure 1:
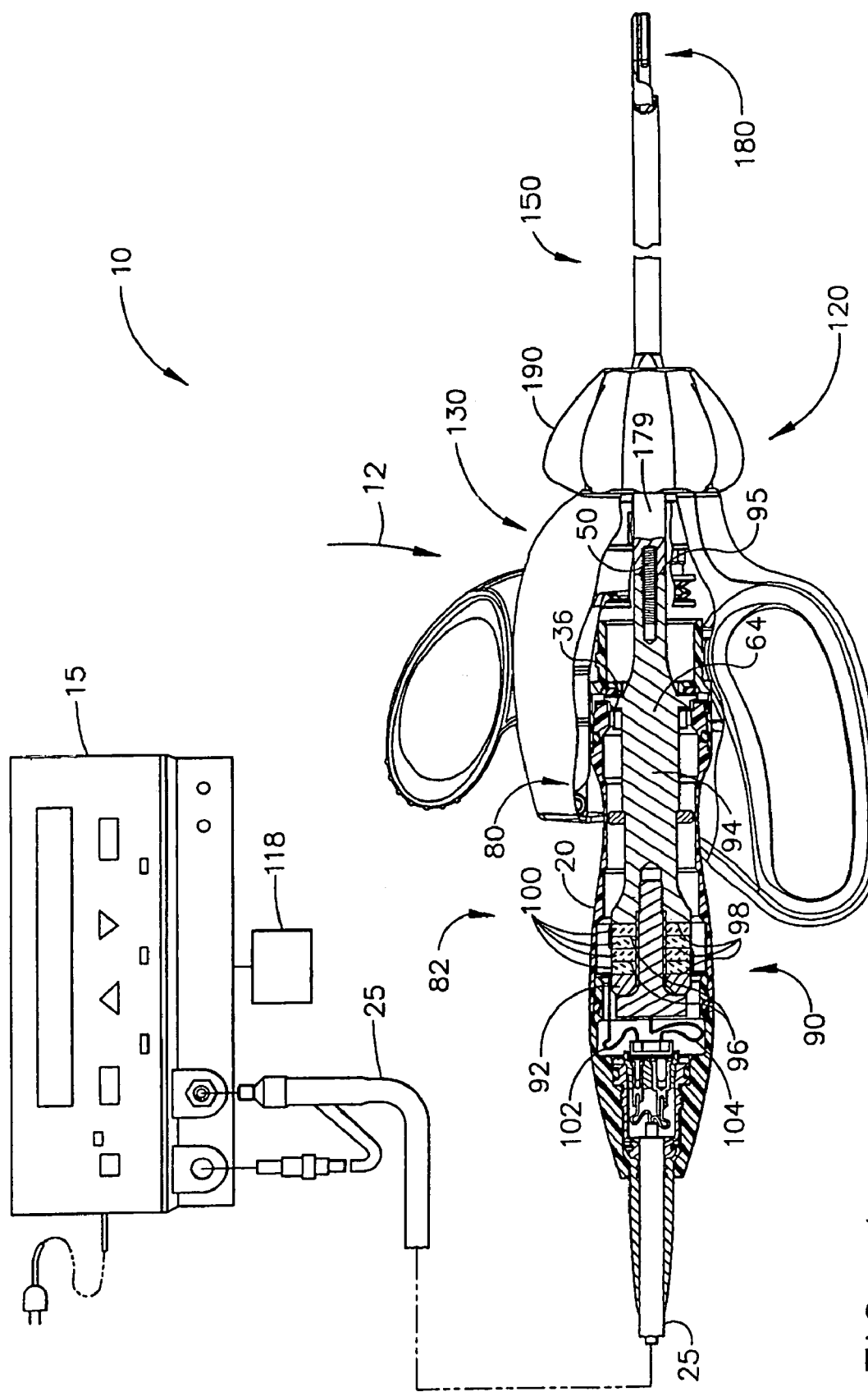
FIG. 1 is a view of the system in accordance with the present invention.

With reference to FIG. 1, an ultrasonic system 10 for use in conjunction with ultrasonic surgical clamping and cutting instruments 12 is disclosed. In accordance with a preferred embodiment of the present invention the ultrasonic system 10 includes an ultrasonic signal generator 15 adapted for applying current and voltage sufficient to maintain power substantially constant during the procedure.

In accordance with a preferred embodiment of the present invention, the system is adapted for working with an ultrasonic instrument 12 similar to that disclosed in U.S. Pat. No. 6,458,142, entitled "Force Limiting Mechanism for an Ultrasonic Surgical Instrument", which is incorporated herein by reference, although the force limiting mechanism of this instrument is not needed in view of the present invention's use of voltage and current in controlling the power applied by the instrument. While a preferred instrument is disclosed in accordance with describing the present invention, those skilled in the art will appreciate that the goal of the present invention is to provide a system adapted for use with a wide range of devices.

For the purpose of disclosing the present invention, the instrument 12 includes sandwich type ultrasonic transducer 82, a handpiece housing 20 and a clamp coagulator 120. The clamp coagulator 120 is used for open or laparoscopic surgery. The ultrasonic transducer 82, which is known as a "Langevin stack", generally includes a transduction portion 90, a first resonator or end-bell 92, a second resonator or fore-bell 94, and ancillary components. An acoustic assembly 80 includes the ultrasonic transducer 82, mount 36, velocity transformer 64 and surface 95.

The distal end of the end-bell 92 is connected to the proximal end of the transduction portion 90, and the proximal end of the fore-bell 94 is connected to the distal end of the transduction portion 90. The fore-bell 94 and end-bell 92 have a length determined by a number of variables, including the thickness of the transduction portion 90, the density and module of elasticity of the material used to manufacture the end-bell 92 and fore-bell 94 and the resonant frequency of the ultrasonic transducer 82. The fore-bell 94 may be tapered inwardly from its proximal end to its distal end to amplify the ultrasonic vibration amplitude as a velocity transformer (not shown) or, alternately, may have no amplification.

The piezoelectric element 100 is preferably manufactured from any suitable material, such as, for example, lead zirconate-titanate, lead meta-niobate, lead-titanate, or other piezoelectric crystal materials. Each of the positive electrodes 96, negative electrodes 98 and piezoelectric elements has a bore extending through the center thereof. The positive and negative electrodes 96, 98 are electrically coupled to first and second wires 102, 104 respectively. The first and second wires 102, 104 are encased within a cable 25 and electrically connectable to the ultrasonic signal generator of the ultrasonic system 10.

In practice, the ultrasonic transducer 82 of the acoustic assembly 80 converts the electrical signal from the ultrasonic signal generator into mechanical energy that results in primarily longitudinal vibratory motion of the ultrasonic transducer 82 and an end-effector 180 at an ultrasonic frequency. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured.

The first and second wires 102, 104 transmit electrical signals from the ultrasonic signal generator 15 to positive electrodes 96 and negative electrodes 98. A suitable generator is available as model number GEN01, from Ethicon Endo-Surgery, Inc., Cincinnati, Ohio. The piezoelectric elements 100 are energized by an electrical signal supplied from the ultrasonic signal generator in response to a foot switch 118 to produce an acoustic standing wave in the acoustic assembly 80. The electrical signal causes disturbances in the piezoelectric element 100 in the form of repeated displacements resulting in large compression forces within the material. The repeated small displacements cause the piezoelectric elements 100 to expand and contract in a continuous manner along the access of the voltage gradient, producing longitudinal waves of ultrasonic energy. The ultrasonic energy is transmitted through the acoustic assembly 80 to the end-effector 180.

In order for the acoustic assembly 80 to deliver energy to the end-effector 180, all components of the acoustic assembly 80 must be acoustically coupled to the ultrasonically active portions of the clamp coagulator 120. The distal end of the ultrasonic transducer 82 may be acoustically coupled at a first surface to the proximal end of the ultrasonic waveguide by a threaded connection, such as a stud 50. The components of the acoustic assembly 80 are preferably acoustically tuned such that the length of any assembly is an integral number of one half wave lengths, where the wavelength lambda is the wavelength of a pre-selected or operating longitudinal vibration drive frequency of the acoustic assembly 80 and where N is any positive integer. It is also contemplated the acoustic assembly 80 may incorporate any suitable arrangement of acoustic elements without departing from the spirit of the present invention.

In an effort to accommodate different force profiles utilized by different surgeons, the present invention controls the power applied by the ultrasonic surgical generator 15 to the instrument 12. The applied nominal power is controlled in an effort to prevent undesired effects to the tissue being clamped and/or cut. By controlling power in accordance with the present invention, the need for mechanical control systems found in prior art ultrasonic instruments is eliminated and improved feedback is provided to the user. Ultimately, the power applied via an ultrasonic instrument 12 is affected by the friction generated between the tissue and the end-effector 180, the velocity of the end-effector and the normal force applied by the end-effector 180. In practice, the friction between the tissue and the end-effector 180 is generally pretty constant with only slight changes due to the dryness of the tissue. The variables in power application are, therefore, the velocity of the end-effector and the applied normal force.

As will be discussed below in detail, the present invention maintains a substantially constant power input by controlling the voltage and current utilized by the ultrasonic surgical instrument 12 based upon the measured impedance through the transducer 82 as it relates to the desired nominal power level. In particular, and with reference to the power profile shown in FIG. 2, the power applied by the ultrasonic surgical instrument 12 is maintained constant after a predetermined pressure level is reached. By continually monitoring the impedance through the transducer 82, which relates to the force being applied by the operator, and adjusting the current passing therethrough, which relates to the velocity of the end-effector 180, such that the nominal power is maintained at a desired level, the present invention is able to provide for a consistent application of power to tissue regardless of the force applied by the operator.

Figure 2:
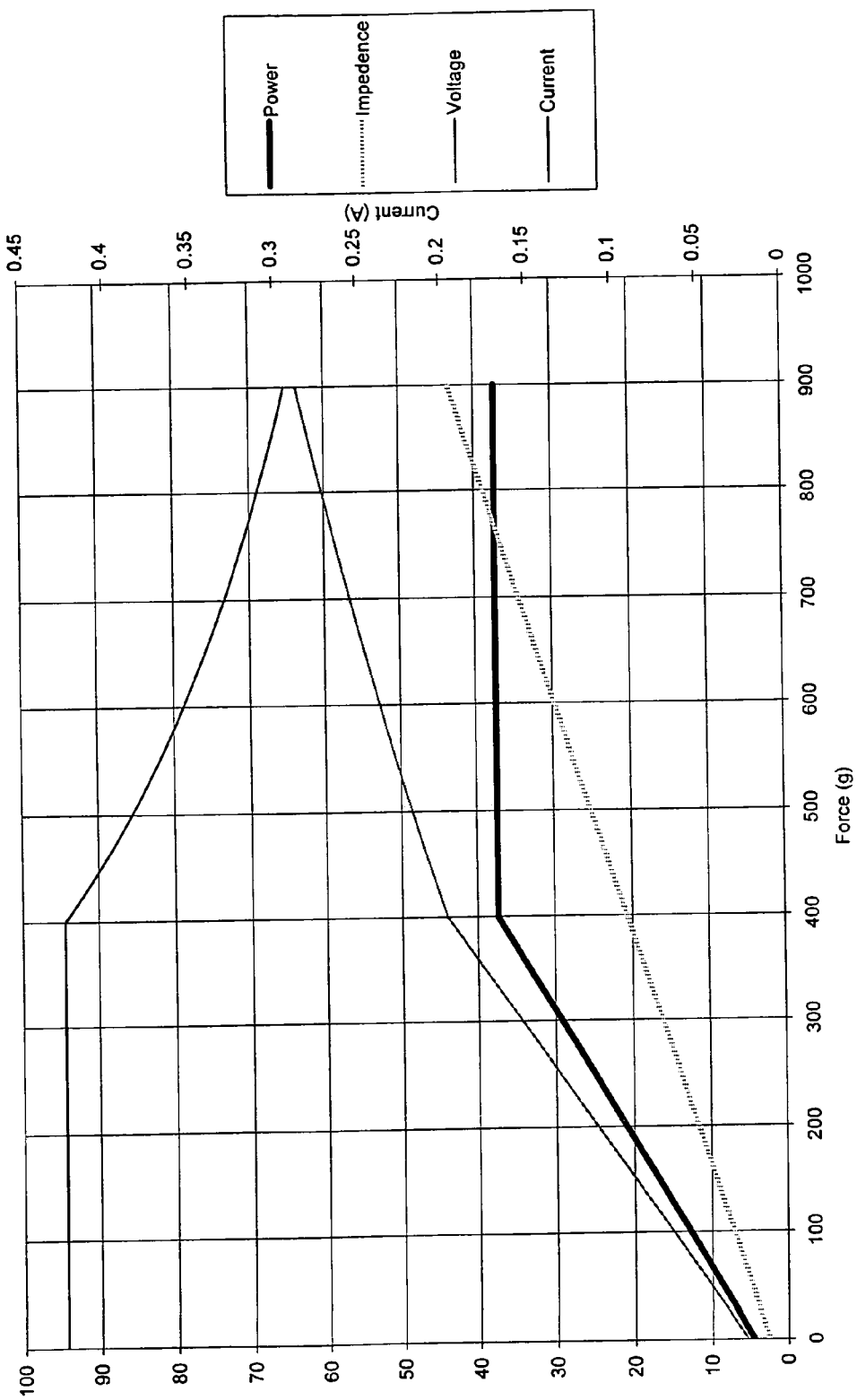
FIG. 2 is a graph showing the current, voltage and power profiles contemplated in accordance with the present invention.

The power produced by the ultrasonic surgical instrument 12 is the product of the voltage and current utilized by the ultrasonic surgical instrument 12 and provided by the ultrasonic surgical generator 15. At force levels applied by the surgeon below 400 grams as shown in FIG. 2, the ultrasonic surgical generator 15 is designed to maintain a certain fixed vibration velocity level at the end effecter 180 of the ultrasonic instrument 12 by maintaining the input current to the transducer. As such, the voltage supplied by the ultrasonic surgical generator 15 of the ultrasonic surgical instrument 12 is proportionally increased as the force applied by the surgeon continues to increase, thereby maintaining a fixed current. As a result, the power up to the 400 grams point in FIG. 2 is increasing continuously. Beyond the 400 grams point, the ultrasonic surgical generator 15 is designed to switch to a mode in which it maintains a certain fixed power into the scalpel and thereby into the target tissue regardless of the force applied by the operator. The voltage while in this mode is increased in such proportion which results in decrease in current as the force applied by the surgeon is increased, but the power is maintained at the same level.

The reduction in current due to varying the proportion by which the voltage is increased results in decreased current flowing thorough the transducer 82 of the ultrasonic surgical instrument 12 and thereby decreased vibration velocity of the end-effecter 180 of the ultrasonic instrument 12. In contrast to prior devices, the voltage is not increased in a manner which will maintain the current, and consequently the vibrations, at a constant level. Rather, the voltage is increased in relation to the current such that the power supplied through the ultrasonic transducer 82 of the ultrasonic surgical instrument 12 is maintained at a constant level. The mechanism for maintaining constant power is achieved by controlling voltage and current, in consideration of the applied force, so as to maintain a constant nominal power. By maintaining power at a constant level, regardless of the applied force, by controlling the voltage and current passing through the ultrasonic surgical instrument 12, the present ultrasonic instrument 12 will apply consistent power regardless of the pressure applied by the surgeon.

As such, and as discussed above, the application of constant power in accordance with the present invention balances vibration (or velocity) levels of the end-effector 180 with the normal pressure applied by the end-effector 180. For example, when a surgeon applies greater normal force via the end-effector 180, the vibration level is reduced and the applied power level remains constant. As those skilled in the art will appreciate, and with reference to the graph presented in FIG. 2, a certain period of ramping up is necessary for utilization of the present system in conjunction with ultrasonic surgical instrument 12. As shown in the FIG. 2, the ramp up occurs as the pressure increases from zero grams force to 400 grams force. During this time, the current is maintained constant while the voltage increases to compensate for the tendency for a reduction in vibrations, and thus current, as the force applied by the surgeon increases.

Once a force of 400 grams is achieved, the voltage and current are regulated to maintain the power at a constant level. As those skilled in the art will appreciate, the power is maintained constant within the force characteristics contemplated for use in accordance with the present invention. The application of force beyond the predetermined limits will result in malfunctioning of the device and surgeons will be warned that an unacceptable force level has been reached.

Figure 3:
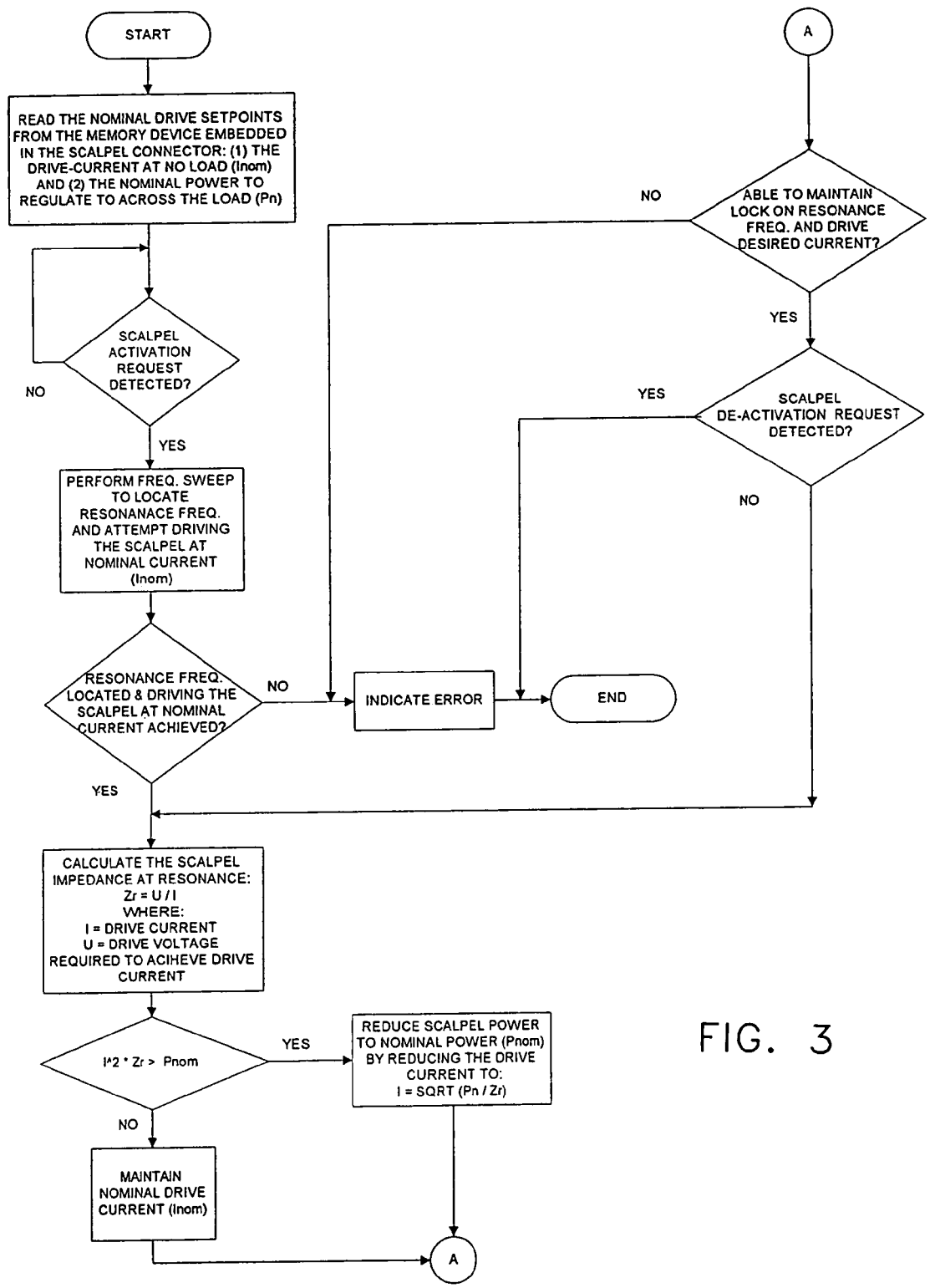
FIG. 3 is a flow chart of a preferred technique for controlling the power level applied to an ultrasonic instrument in accordance with the present invention.

More particularly, and with reference to FIG. 3, a flow chart presenting a preferred operating procedure is disclosed. In accordance with the present invention, the ultrasonic surgical instrument 12 and the ultrasonic surgical generator 15 are started. The ultrasonic surgical generator 15, via its operating processor, reads the nominal drive set points from a memory device embedded in the ultrasonic instrument 12. In particular, the following set points are read: the drive current at no load (that is, the nominal current $I_{nom}$) and the nominal power ($P_{nom}$) to regulate to across the load (that is, the predetermined power at which the instrument is designed for operation in accordance with the present invention).

Thereafter, it is determined whether instrument activation has been requested by the operator. If the answer is NO, the instrument 12 returns to activation requested status awaiting a request for activation. If activation of the instrument is requested by the operator, a frequency sweep is performed to locate resonance frequencies of the instrument 12 and to attempt driving the instrument at nominal current ($I_{nom}$). The ultrasonic surgical generator 15 then determines whether the resonance frequency is located and whether the instrument is capable of being driven at nominal current ($I_{nom}$). If the ultrasonic surgical generator 15 fails to either locate the resonance frequency or drive the scalpel at nominal current ($I_{nom}$), an error is indicated and the ultrasonic surgical generator 15 shuts down. If the resonance frequency is located and the instrument operates at nominal current levels ($I_{nom}$), the scalpel impedance ($Z_r$) at the resonance frequency is calculated. This is achieved utilizing the following formula:

$$Z_r = V \div I$$

where,
I=drive current (which is initially $I_{nom}$), and
V=drive voltage required to achieve drive current.

The system then determines whether the power, calculated as $I^2 \times Z_r$, is greater than the nominal power ($P_{nom}$) to regulate across the load. If it is determined that the nominal power ($P_{nom}$) to regulate across the load is less than $I^2 \times Z_r$, the power being applied by the instrument is considered to be too high and the instrument power is reduced to nominal power ($P_{nom}$) by reducing the drive current to I=SQRT ($P_{nom}/Z_r$). As those skilled in the art will appreciate, the drive current is simply adjusted by altering the drive voltage.

Thereafter, the ultrasonic surgical generator 15 determines whether it is able to maintain the lock on the resonance frequency and to drive at the desired current. If the answer is NO, an error is indicated and the procedure ends. If the ultrasonic surgical generator is able to maintain a lock on the resonance frequency and drive at the desired current, the ultrasonic surgical generator 15 checks to see if a deactivation request is detected, and if no deactivation request is detected, the ultrasonic surgical generator 15 returns to the step of calculating the scalpel impedance ($Z_r$) at the resonance frequency.

If the nominal power ($P_{nom}$) is greater than $I^2 \times Z_r$, the nominal drive current ($I_{nom}$) is maintained and the system determines whether it is able to maintain a lock on the resonance frequency and the drive at the desired current. If the answer is NO, an error is indicated and the procedure ends. If the answer is YES, the ultrasonic surgical generator 15 determines whether any deactivation requests have been detected, and if none are detected, the ultrasonic surgical generator 15 returns to the step of calculating the scalpel impedance ($Z_r$) at the resonance frequency.

This procedure is continually repeated during the surgical procedure to maintain a nominal desired power level and to operate the system in accordance with the present invention. By continually monitoring the impedance through the transducer 82, which relates to the force being applied by the operator, and adjusting the current passing therethrough, which relates to the velocity of the end-effector 180, such that the nominal power is maintained at a desired level the present invention is able to provide for a consistent application of power regardless of the force applied by the operator.

While the preferred embodiments have been shown and described, it will be understood that there is no intent to limit the invention by such disclosure, but rather, is intended to cover all modifications and alternate constructions falling within the spirit and scope of the invention.

The invention claimed is:
1. An ultrasonic surgical system, comprising:
an instrument and an ultrasonic signal generator linked to the instrument for supplying a desired signal to the instrument, the instrument includes an ultrasonic transducer, a housing and an end-effector;

the ultrasonic signal generator includes a control system, the control system includes a generator supplying electrical energy to the instrument, the electrical energy supplied by the generator being controlled such that power applied by the instrument is maintained constant once a predetermined pressure threshold is met.

2. The ultrasonic surgical system according to claim 1, wherein the power applied by the instrument is equal to the product of the current and voltage generated by the generator.

3. The ultrasonic surgical system according to claim 2, further including means for measuring impedance passing through the instrument and controlling the power level based upon the measured impedance.

4. The ultrasonic surgical system according to claim 3, wherein the means for controlling the power level includes adjusting current passing through the instrument based upon the measured impedance.

5. The ultrasonic surgical system according to claim 1, wherein voltage supplied by the generator is increased as the force applied continues to increase.

6. The ultrasonic surgical system according to claim 3, further including means for measuring impedance passing through the instrument and controlling the power level based upon the measured impedance.

7. The ultrasonic surgical system according to claim 6, wherein the means for controlling the power level includes adjusting current passing through the instrument based upon the measured impedance.

8. The ultrasonic surgical system according to claim 1, further including means for balancing vibration levels of the instrument with pressure applied by the instrument.

* * * * *